(12) United States Patent
Jin et al.

(10) Patent No.: US 9,445,782 B2
(45) Date of Patent: Sep. 20, 2016

(54) ULTRASONIC PROBE AND MANUFACTURING METHOD THEREOF

(71) Applicant: SAMSUNG MEDISON CO., LTD., Gangwon-Do (KR)

(72) Inventors: Gil Ju Jin, Seoul (KR); Mi Ri Kim, Seoul (KR); Jae-Yk Kim, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 75 days.

(21) Appl. No.: 13/772,195

(22) Filed: Feb. 20, 2013

(65) Prior Publication Data
US 2013/0231566 A1    Sep. 5, 2013

(30) Foreign Application Priority Data
Feb. 20, 2012  (KR) .................. 10-2012-0017002

(51) Int. Cl.
  *A61B 8/00*  (2006.01)
  *B06B 1/06*  (2006.01)
(52) U.S. Cl.
  CPC .. *A61B 8/42* (2013.01); *B06B 1/06* (2013.01)
(58) Field of Classification Search
  CPC ................................. A61B 8/42; B06B 1/06
  USPC ....... 600/300, 407, 424, 437, 440, 443, 447, 600/459, 472; 310/311, 322, 327, 334, 335; 361/749, 760, 777
  See application file for complete search history.

(56) References Cited

U.S. PATENT DOCUMENTS

| 2003/0085635 | A1* | 5/2003 | Davidsen | B06B 1/0607 310/334 |
| 2008/0303381 | A1* | 12/2008 | Yuuya | C08K 3/22 310/327 |
| 2010/0241004 | A1* | 9/2010 | Jung | B06B 1/0622 600/459 |

FOREIGN PATENT DOCUMENTS

| KR | 10-2010-0047394 A | 5/2010 |
| KR | 10-2010-0104534 A | 9/2010 |

OTHER PUBLICATIONS

Korean Office Action issued in Korean Patent Application No. KR 10-2012-0017002 dated Jul. 1, 2013.

* cited by examiner

*Primary Examiner* — Tse Chen
*Assistant Examiner* — Charles G Chiang
(74) *Attorney, Agent, or Firm* — McDermott Will & Emery LLP

(57) ABSTRACT

The present application relates to an ultrasonic probe including a connector capable of applying an electrical signal to a piezoelectric material and disposed at the outside of a backing layer, and a method of manufacturing the same. The ultrasonic probe includes a piezoelectric material, a backing layer installed on the rear surface of the piezoelectric material, and a first connector installed on at least one side surface of the backing layer and electrically connected to the piezoelectric material.

11 Claims, 14 Drawing Sheets

ULTRASONIC PROBE AND
MANUFACTURING METHOD THEREOF

CROSS-REFERENCE TO RELATED
APPLICATION

This application claims priority to Korean Patent Application No. 2012-0017002, filed on Feb. 20, 2012 in the Korean Intellectual Property Office, the disclosure of which is incorporated herein by reference in its entirety.

TECHNICAL FIELD

The present application relates to an ultrasonic probe to generate an image of an internal state of an object using ultrasound.

BACKGROUND

An ultrasonic diagnosis apparatus irradiates an ultrasonic signal toward a target region of the interior of a body of an object from the surface of the body of the object, and non-invasively acquires an image regarding a soft tissue tomogram or a blood stream using information of a reflected ultrasonic signal (e.g., an ultrasonic echo signal).

The ultrasonic diagnosis apparatus is small and inexpensive, executes display in real time and has high safety without radiation exposure, as compared to other image diagnosis apparatuses, such as an X-ray diagnosis apparatus, an X-ray computerized tomography (CT) scanner, a magnetic resonance image (MRI), and a nuclear medicine diagnosis apparatus, and is thus widely used for heart diagnosis, celiac diagnosis, urinary diagnosis, and obstetrical diagnosis.

The ultrasonic diagnosis apparatus includes an ultrasonic probe for transmitting an ultrasonic signal to an object and receiving an ultrasonic echo signal reflected by the object to acquire an ultrasonic image of the object.

The ultrasonic probe includes a piezoelectric layer in which a piezoelectric material vibrates to execute a conversion between an electrical signal and an acoustic signal. A matching layer reduces an acoustic impedance difference between the piezoelectric layer and the object so as to maximally transmit ultrasonic waves generated in the piezoelectric layer to the object. A lens concentrates ultrasonic waves proceeding in the forward direction of the piezoelectric layer on a predetermined point. A backing layer prevents ultrasonic waves from proceeding in the backward direction of the piezoelectric layer to prevent image distortion.

SUMMARY

Therefore, it is an aspect of the present application to provide an ultrasonic probe including a connector capable of applying an electrical signal to a piezoelectric material and disposed at the outside of a backing layer and a method of manufacturing the same.

Additional aspects of the application will be set forth in part in the description which follows and, in part, will be obvious from the description, or may be learned by practice of the subject matter described herein.

In accordance with one aspect of the present application, an ultrasonic probe includes a piezoelectric material. A backing layer is installed on the rear surface of the piezoelectric material. A first connector is installed on at least one side surface of the backing layer and is electrically connected to the piezoelectric material.

The ultrasonic probe may further include a first electrode layer formed on the front surface of the backing layer, and the first electrode layer may be electrically connected to the first connector.

The piezoelectric material may include an electrode disposed on at least one surface of the piezoelectric material including the rear surface of the piezoelectric material and electrically connected to the first electrode layer.

The ultrasonic probe may further include a first supporter installed on the first connector to support the first connector by fixing the first connector to one side surface of the backing layer.

The first supporter may be installed to protrude from the front surface of the backing layer and forms a mounting groove, at which the piezoelectric material is installed.

The first supporter may be formed of an insulating material.

The ultrasonic probe may further include a second electrode layer disposed on the front surface of the first supporter.

The piezoelectric material may include an electrode disposed on at least one surface of the piezoelectric material including the front surface of the piezoelectric material and electrically connected to the second electrode layer.

The ultrasonic probe may further include a second connector spaced apart from the first connector and electrically connected to the piezoelectric material.

The second connector may be installed on the first supporter to protrude from the front surface of the backing layer with the first supporter.

The ultrasonic probe may further include a second supporter installed on the second connector to support the second connector by fixing the second connector to one side surface of the backing layer, and the second supporter may be formed of an insulating material.

The ultrasonic probe may further include a second electrode layer disposed on the front surface of the first supporter and electrically connected to the second connector.

The piezoelectric material may include an electrode disposed on at least one surface of the piezoelectric material including the front surface of the piezoelectric material and electrically connected to the second electrode layer.

The ultrasonic probe may further include a second connector spaced apart from the first connector and electrically connected to the piezoelectric material.

The ultrasonic probe may further include a second supporter installed on the second connector to support the second connector by fixing the second connector to one side surface of the backing layer, and the second supporter may be formed of an insulating material.

The first connector and the second connector may include a flexible printed circuit board (FPCB), a printed circuit board (PCB), or a wire.

The ultrasonic probe may further include a second electrode layer disposed on the front surface of the backing layer, and the second electrode layer may be electrically connected to the second connector.

The piezoelectric material may include an electrode disposed on at least one surface of the piezoelectric material including the rear surface of the piezoelectric material and electrically connected to the second electrode layer.

The ultrasonic probe may further include a first electrode layer disposed on the front surface of the backing layer and electrically connected to the first connector, and the first electrode layer may be separated from the second electrode layer.

According to an aspect of the present application, the electrode disposed on the front surface of the backing layer enlarges a contact area between the connector and the piezoelectric material, thereby providing excellent electrical connection properties.

Furthermore, connection between the piezoelectric material and the connector may be easily performed, and performance degradation caused by defective connection.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

These and/or other aspects of the application will become apparent and more readily appreciated from the following description of the examples, taken in conjunction with the accompanying drawings of which.

DETAILED DESCRIPTION

Figure 1:
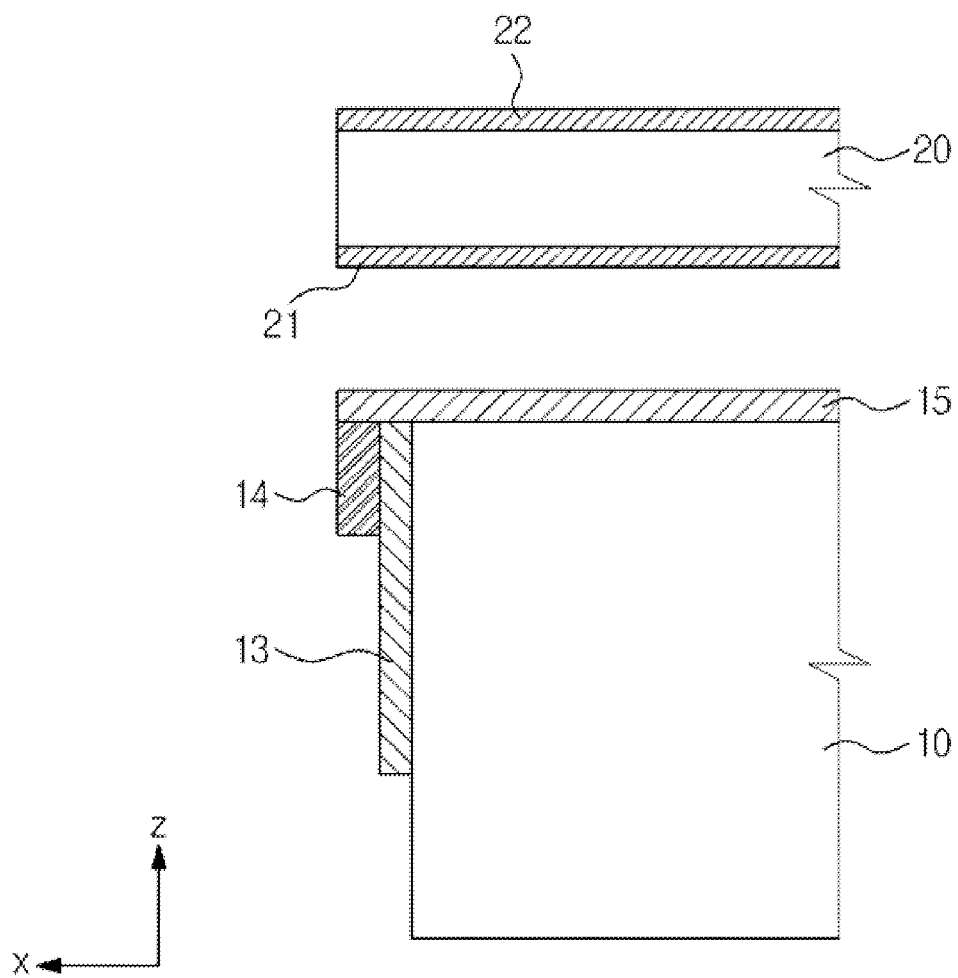
FIG. 1 is a cross-sectional view illustrating an ultrasonic probe according to one example of the present application.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Reference will now be made in detail to the examples of the present application which are illustrated in the accompanying drawings, wherein like reference numerals refer to like elements throughout.

Hereinafter, an ultrasonic probe and a method of manufacturing the same will be described.

Figure 2:
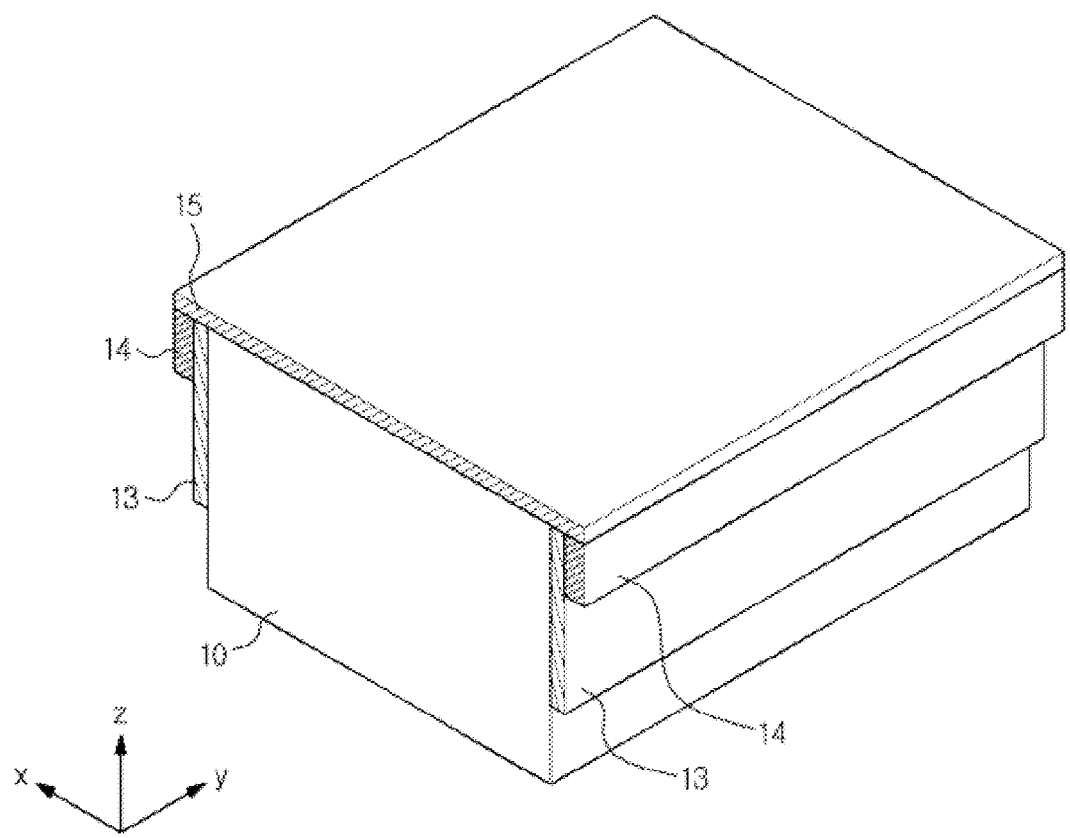
FIG. 2 is a perspective view illustrating a backing layer of the ultrasonic probe of FIG. 1.

FIG. 1 is a cross-sectional view illustrating an ultrasonic probe according to one example. FIG. 2 is a perspective view illustrating a backing layer 10 of the ultrasonic probe of FIG. 1.

Figure 3:
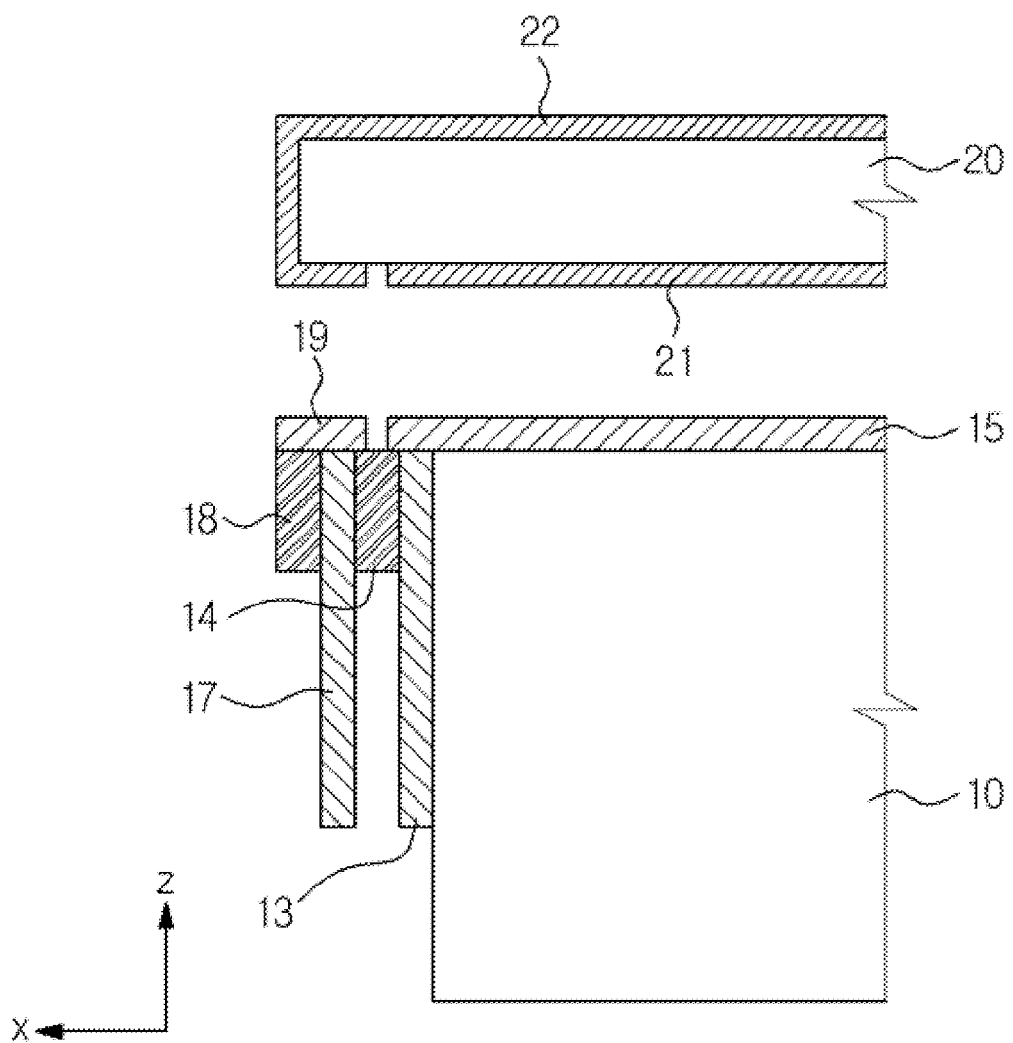
FIG. 3 is a cross-sectional view illustrating an ultrasonic probe according to another example.
Figure 4:
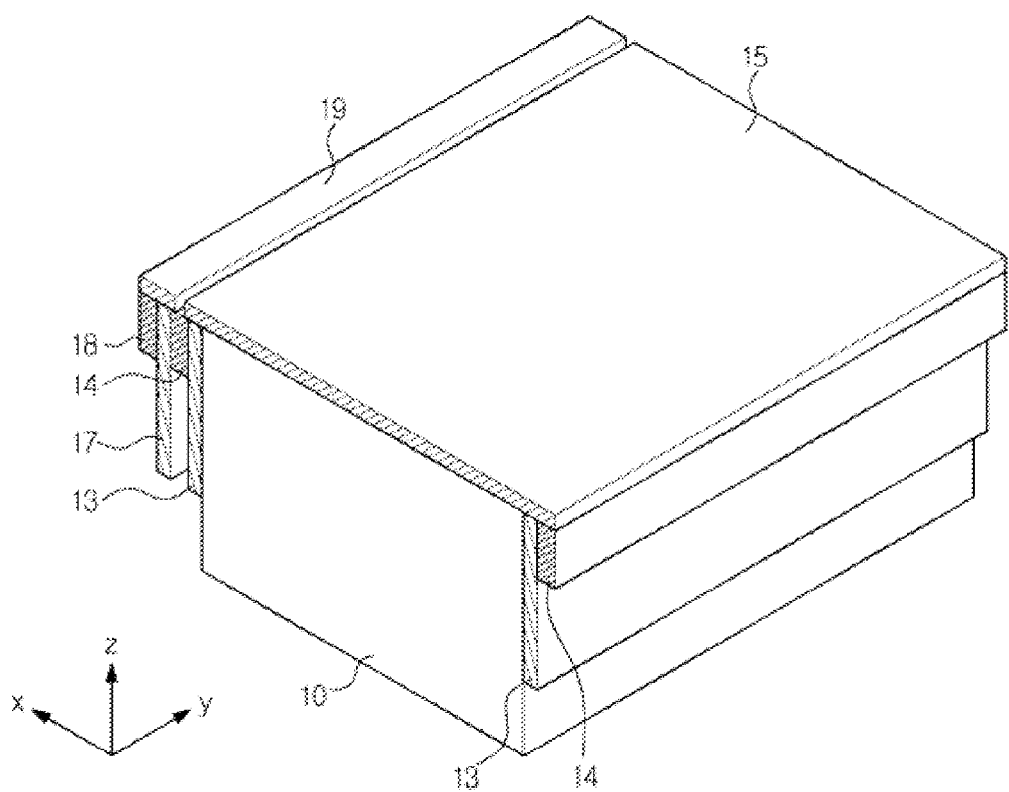
FIG. 4 is a perspective view illustrating a backing layer of the ultrasonic probe of FIG. 3.
Figure 5:
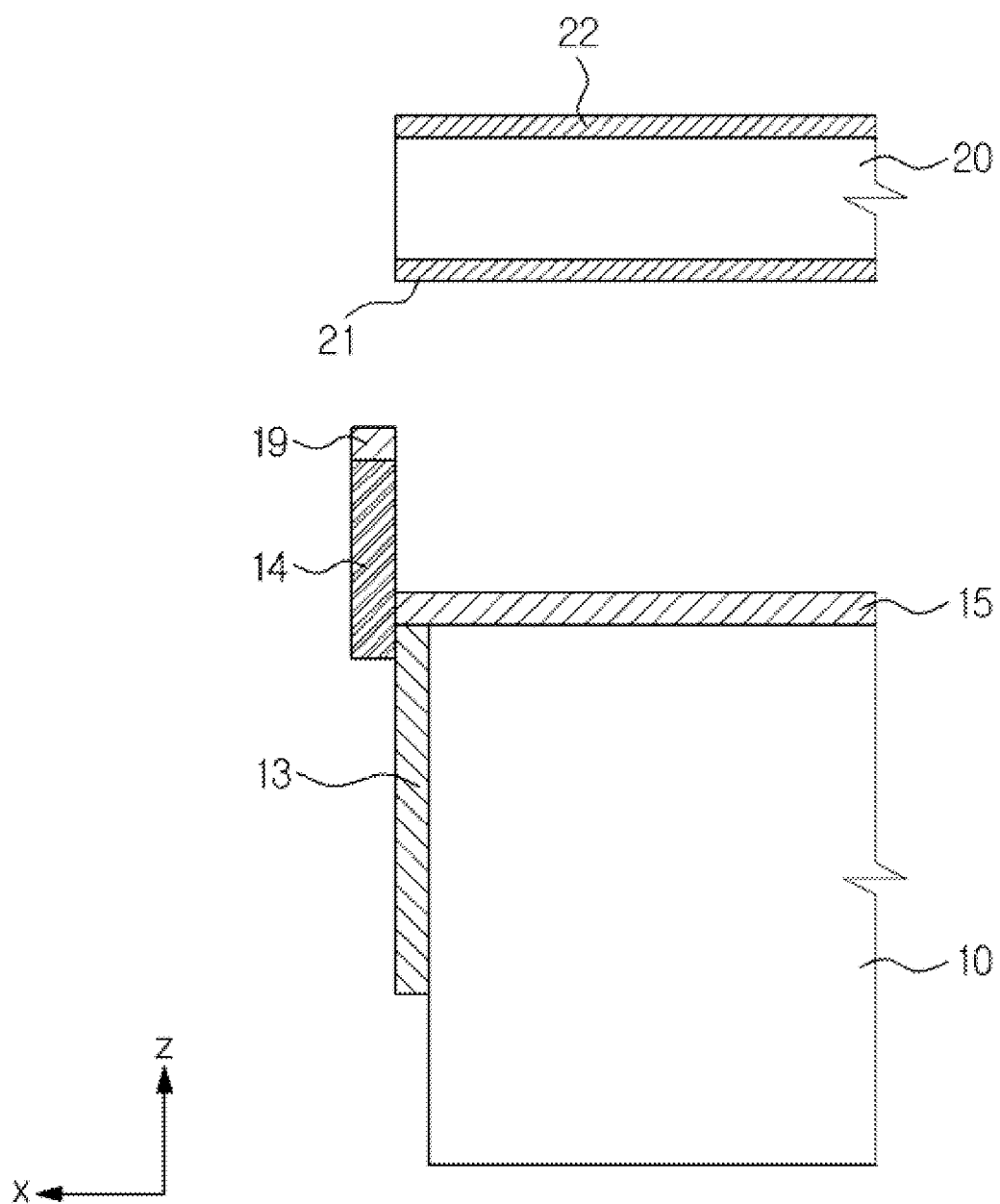
FIG. 5 is a cross-sectional view illustrating an ultrasonic probe according to another example of the present application.
Figure 6:
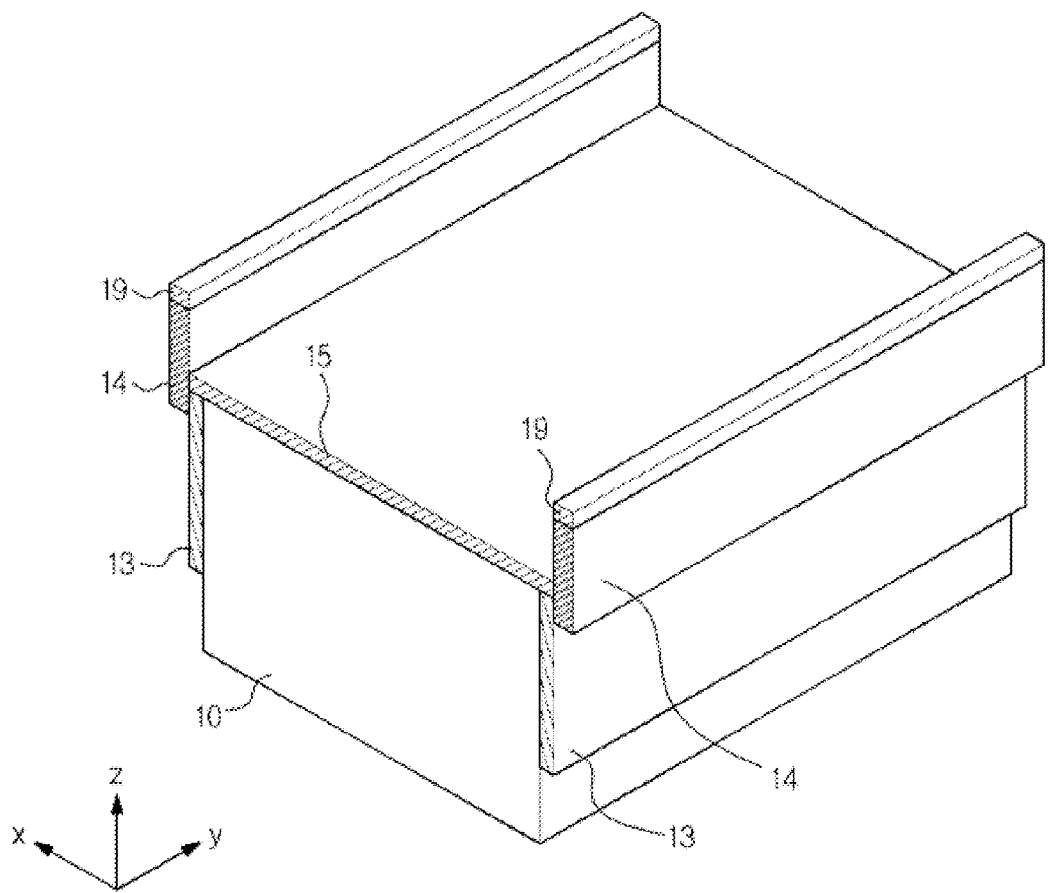
FIG. 6 is a perspective view illustrating a backing layer of the ultrasonic probe of FIG. 5.

FIG. 3 is a cross-sectional view illustrating an ultrasonic probe according to another example. FIG. 4 is a perspective view illustrating a backing layer 10 of the ultrasonic probe of FIG. 3, FIG. 5 is a cross-sectional view illustrating an ultrasonic probe according to another example. FIG. 6 is a perspective view illustrating a backing layer 10 of the ultrasonic probe of FIG. 5.

Figure 7:
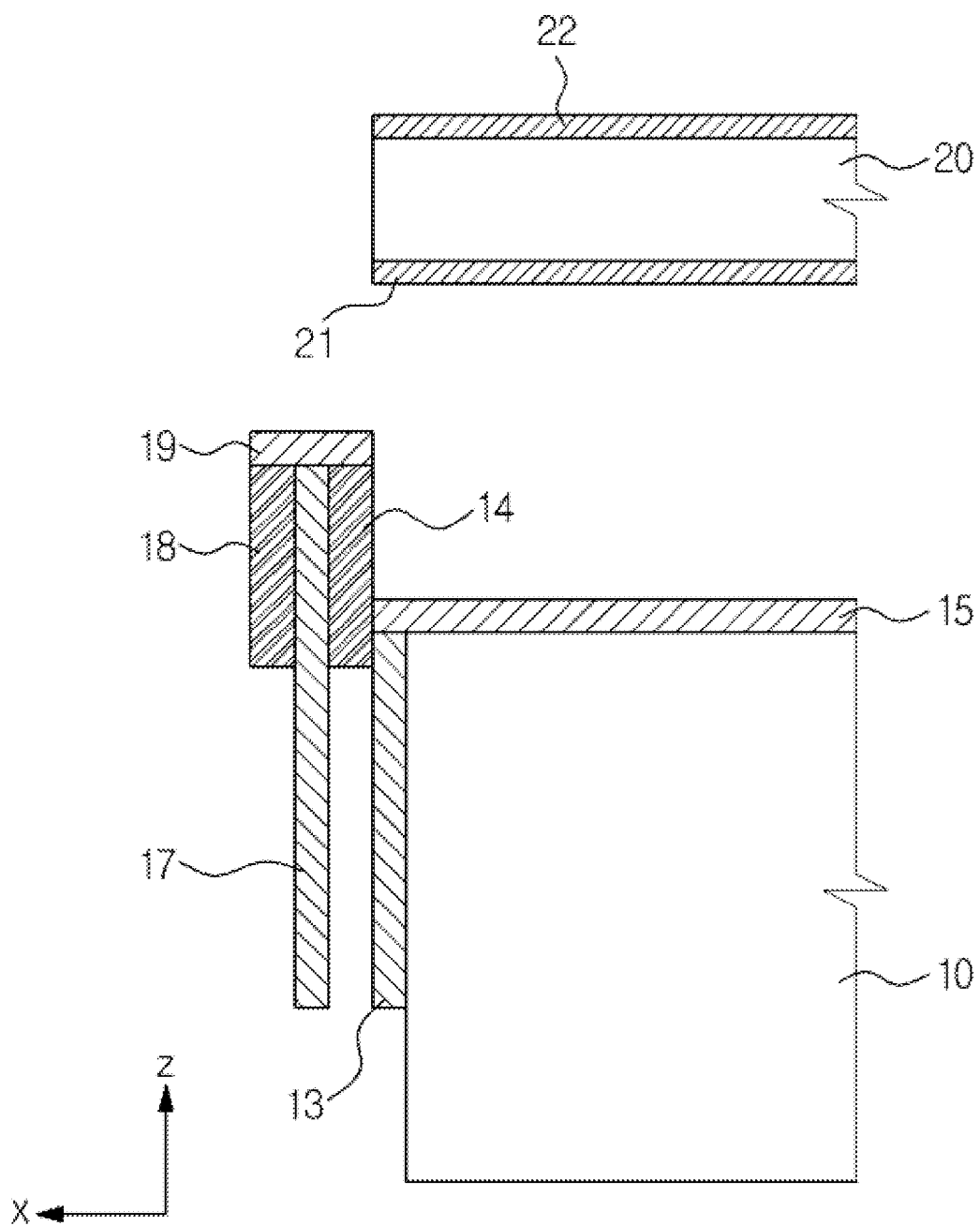
FIG. 7 is a cross-sectional view illustrating an ultrasonic probe according to another example of the present application.
Figure 8:
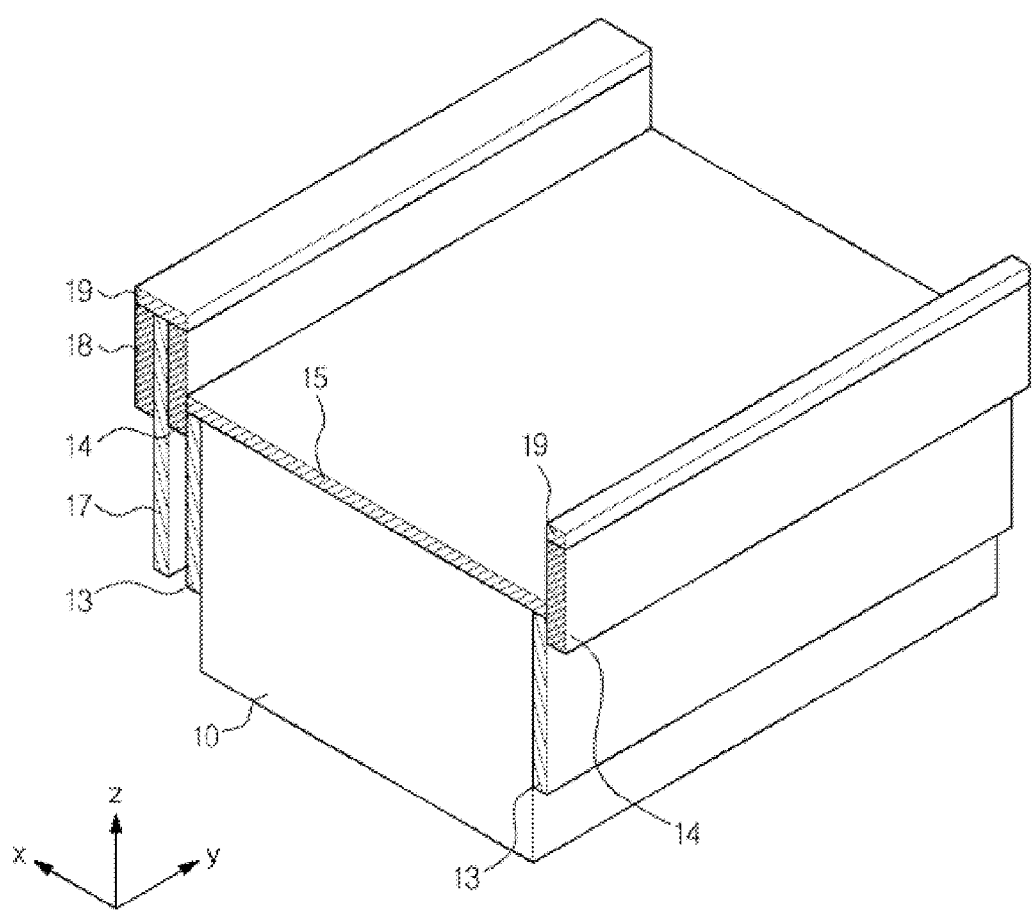
FIG. 8 is a perspective view illustrating a backing layer of the ultrasonic probe of FIG. 7.

FIG. 7 is a cross-sectional view illustrating an ultrasonic probe according to another example. FIG. 8 is a perspective view illustrating a backing layer 10 of the ultrasonic probe of FIG. 7.

The ultrasonic probe according to an example includes a piezoelectric layer 20, a backing layer 10 installed on the rear surface of the piezoelectric layer 20, and a first connector 13 installed on at least one side surface of the backing layer 10.

The effect of voltage generation in a designated material in response to applied mechanical pressure and the effect of mechanical deformation in response to applied voltage are respectively referred to as the piezoelectric effect and inverse piezoelectric effect. A material exhibiting such effects is referred to as a piezoelectric material.

That is, the piezoelectric material is a material which converts electrical energy into mechanical vibration energy or converts mechanical vibration energy into electrical energy.

The ultrasonic probe according to one example includes the piezoelectric layer 20 formed of a piezoelectric material that generates ultrasonic waves in response to an electrical signal applied thereto by converting the electrical signal into mechanical vibration.

The piezoelectric material constituting the piezoelectric layer 20 may include PZMT single crystals formed of lead zirconate titanate (PZT) ceramics, a solid solution of lead magnesium niobate, and lead titanate or PZNT single crystals formed of a solid solution of lead zinc niobate and lead titanate.

In addition, the piezoelectric layer 20 may have a single-layered or multi-layered stack structure.

In general, impedance and voltage are easily controlled in the piezoelectric layer 20 having a stack structure, so that excellent sensitivity, a high energy conversion rate, and soft spectrum may be obtained.

In addition, electrodes to which electrical signals are applied may be disposed on the front and rear surfaces of the piezoelectric layer 20. When the electrodes are disposed on the front and rear surfaces of the piezoelectric layer 20, one of the electrodes disposed on the front and rear surfaces may be a ground electrode and the other may be a signal electrode.

The electrode may be formed of a highly conductive metal such as gold, silver, or copper by techniques such as deposition, sputtering, plating, or spraying.

Although not shown in the drawings, a matching layer may be installed on the front surface of the piezoelectric layer 20. The matching layer reduces an acoustic impedance difference between the piezoelectric layer 20 and an object to match acoustic impedances of the piezoelectric layer 20 and the object. Thus, ultrasonic waves generated in the piezoelectric layer 20 are effectively transmitted to the object.

For this, the matching layer may have a middle value between the acoustic impedances of the piezoelectric layer 20 and the object.

The matching layer may be formed of a glass or resin material. In addition, a plurality of matching layers may be formed, and the matching layers may be formed of different materials in order to change the acoustic impedance stepwise from the piezoelectric layer 20 to the object.

The piezoelectric layer 20 and the matching layer may be processed in a two-dimensional matrix array or in a one-dimensional array by a dicing process to be used as a multi-channel.

In addition, a protective layer (not shown) may be disposed on the front surface of the matching layer. The protective layer may be an RE shield capable of preventing leakage of a high-frequency component generated in the piezoelectric layer 20 to the outside and blocking inflow of an external high-frequency signal.

Furthermore, the protective layer may be formed by coating a conductive material on a surface of a film having moisture resistance and chemical resistance and may be a C/S film capable of protecting internal parts from water and chemicals used in disinfection, and the like.

Also, a lens (not shown) may be disposed on the front surface of the matching layer. The lens may have a convex shape in an ultrasound-radiating direction so as to concentrate the ultrasonic waves. Alternatively, the lens may have a concave shape if the speed of sound is less than that in the human body.

The backing layer 10 is disposed on the rear surface of the piezoelectric layer 20. The backing layer 10 absorbs and scatters ultrasonic waves generated in the piezoelectric layer 20 and proceeding in the backward direction of the piezoelectric layer 20. Accordingly, image distortion may be prevented.

The backing layer 10 may be fabricated in a multi-layered structure in order to improve ultrasonic wave attenuation or blocking effects. In addition, the backing layer 10 may be formed of a rubber-containing material to which an epoxy resin and a tungsten powder are added.

As shown in the examples of FIGS. 1 and 2, the first connector 13 is installed on at least one side surface of the backing layer 10.

Figure 9:
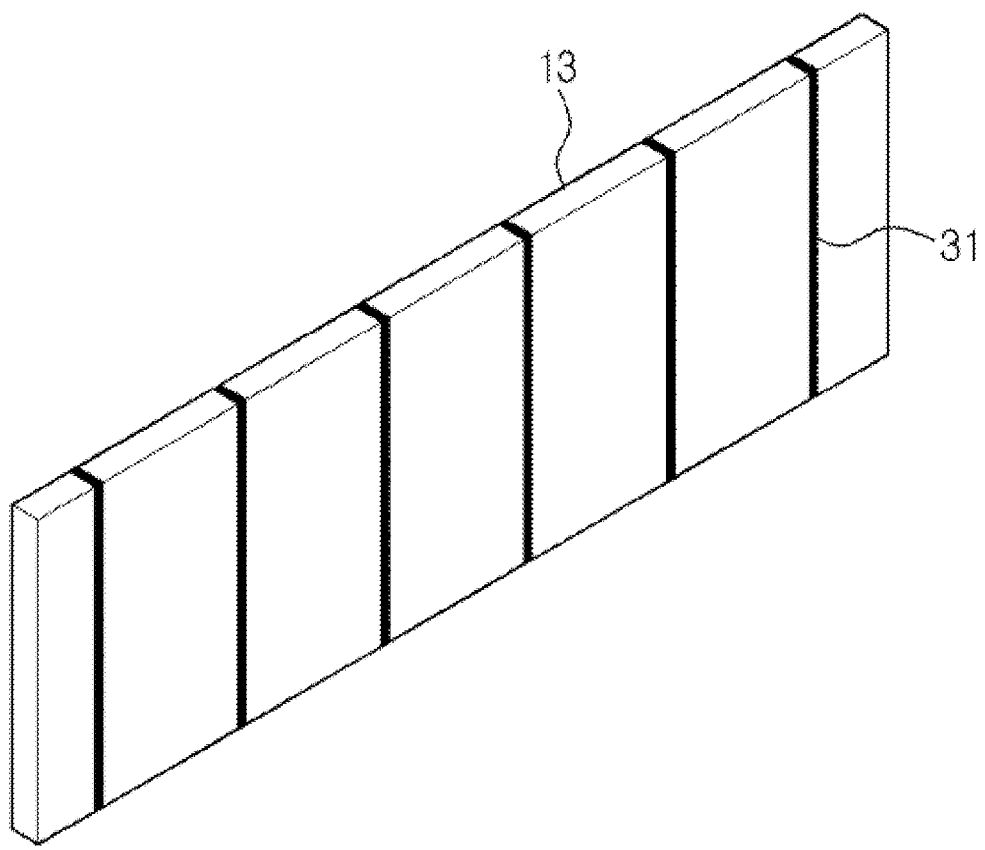
FIG. 9 is a perspective view illustrating a first connector according to yet another example of the present application.

The first connector 13 may include an insulator and an electrode 31. The electrode 31 may include a plurality of electrodes disposed on the insulator. As shown in FIG. 9, each of the electrodes 31 extends in the z-axis direction. One end of each electrode 31 is exposed through the front surface of the backing layer 10 to be electrically connected to a first electrode layer 15 disposed on the front surface of the backing layer 10. The electrodes 31 may be arranged in the y-axis direction to be spaced apart from each other by a predetermined interval.

According to the example, the electrode 31 provided on the first connector 13 is a signal electrode that is electrically connected to the first electrode layer 15 of the backing layer 10 and applies an electrical signal to the piezoelectric layer 20.

After processing of the piezoelectric layer 20 into an array, the number of the electrodes 31 and the interval therebetween may be determined such that each of the electrodes 31 respectively corresponds to each of the elements constituting the array.

The first connector 13 may be installed on at least one side surface of the backing layer 10. In FIG. 2, the first connectors 13 are installed on both side surfaces of the backing layer 10. However, the first connector 13 may be installed on one side surface of the backing layer 10.

If the first connectors 13 are installed on both side surfaces of the backing layer 10, the electrodes 31 of the first connector 13 provided on the left side surface and the electrodes 31 of the first connector 13 provided on the right side surface may be aligned alternately with respect to each other.

Figure 10:
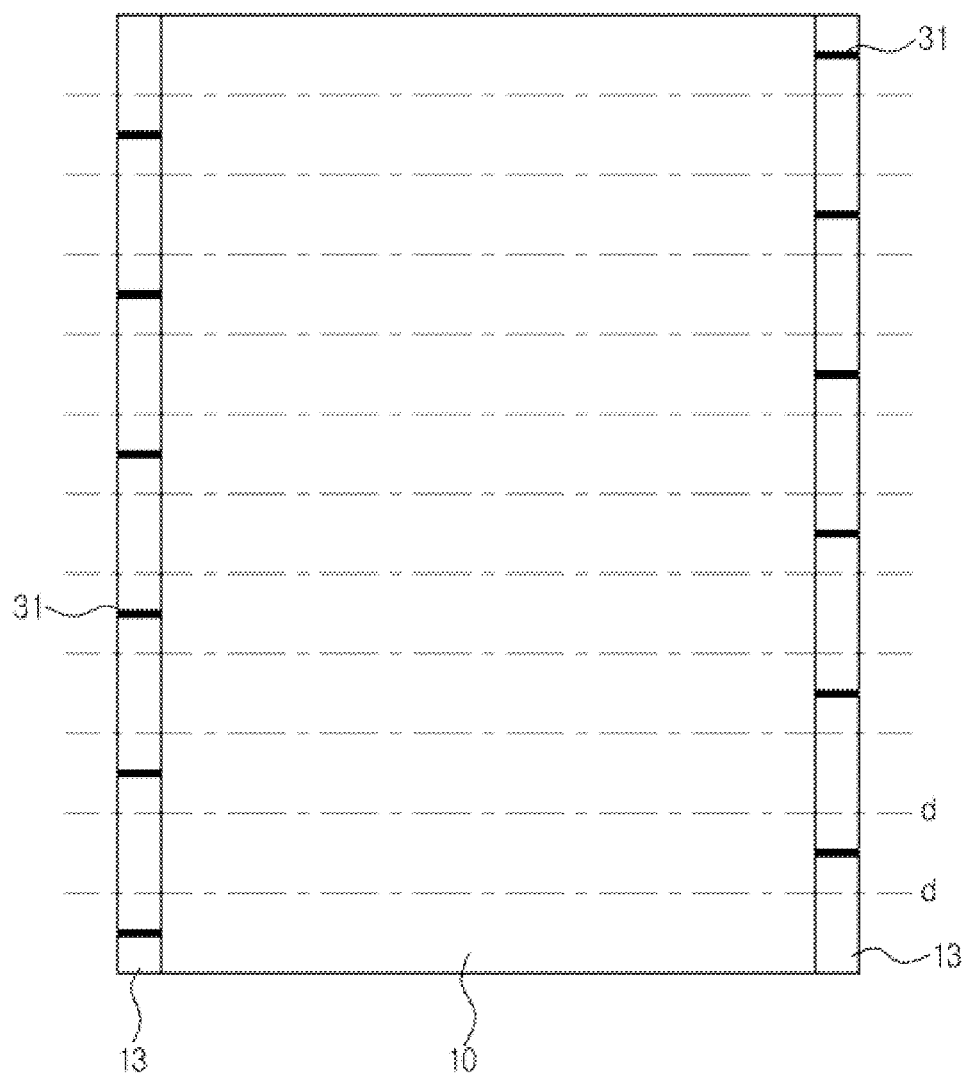
FIG. 10 is a top view of a backing layer according to an example of the present application.

Referring to FIG. 10, the electrodes 31 of the first connector 13 provided on the left side surface are aligned alternately with respect to the electrodes 31 of the first connector 13 provided on the right side surface.

FIG. 10 is a top view of the backing layer 10 before the piezoelectric layer 20 is installed. In FIG. 10, the first electrode layer 15 and a supporter, shown in FIGS. 1 and 2, are not illustrated.

As shown in FIG. 10, if the electrodes 31 of the first connectors 13 provided on both side surfaces of the backing layer 10 are aligned alternately with respect to each other, the first connectors 13 are diced along separation lines d shown in FIG. 10 when the piezoelectric layer 20 is installed on the front surface of the backing layer 10 and divided into an array by a dicing process later. Accordingly, each of the electrodes 31 of the first connectors 13 disposed on the left and right side surfaces of the backing layer 10 may be electrically connected to each of the elements of the piezoelectric layer 20.

The first connector 13 may include a flexible printed circuit board (FPCB). The first connector 13 may also include a PCB or other known elements capable of supplying an electrical signal.

In addition, a first supporter 14, which supports the first connector 13 on one side surface thereof, may be disposed on the first connector 13 to fix the first connector 13 to one side surface of the backing layer 10.

The first supporter 14 may be formed of an insulating material. Different from the backing layer, the first supporter 14 may be preferably formed of a material that does not have the sound absorbing property, or formed of a material having a significantly low level of absorbing property even if formed of the sound absorbing property.

In addition, the first electrode layer 15, which is electrically connected to the first connector 13 installed on the side surface of the backing layer 10, may be disposed on the front surface of the backing layer 10. A first electrode 21, which is electrically connected to the first electrode layer 15 disposed on the front surface of the backing layer 10, may be disposed on the rear surface of the piezoelectric layer 20.

Thus, the first electrode layer 15 is electrically connected to the first electrode 21 disposed on the rear surface of the piezoelectric layer 20, so that an electrical signal provided from the first connector 13 may be transmitted to the piezoelectric layer 20. Since the electrode of the first connector 13 is a signal electrode, the first electrode 21 disposed on the rear surface of the piezoelectric layer 20 constitutes a signal electrode (or positive electrode), and an electrode to be disposed on the front surface of the piezoelectric layer 20 constitutes a ground electrode (or negative electrode).

The first electrode layer 15 may be disposed on the front surface of the backing layer 10 using a conductive material such as gold, silver, or copper by a technique such as coating, deposition, sputtering, plating, or spraying.

FIGS. 3 and 4 illustrate an ultrasonic probe according to another example. Referring to FIGS. 3 and 4, a first connector 13 and a second connector 17 are installed on at least one side surface of the backing layer 10.

FIGS. 3 and 4 illustrate that the first connectors 13 are installed on both side surfaces of the backing layer 10, as shown in FIGS. 1 and 2. However, the first connector 13 may be installed on one side surface of the backing layer 10.

The first connector 13 is the same as that of FIGS. 1 and 2, and thus a detailed description thereof is omitted.

In the ultrasonic probe according to the present example, the second connector 17 is further installed on at least one side surface of the backing layer 10. The second connector 17 is installed to be spaced apart from the first connector 13 by a predetermined interval.

By installing the second connector 17 on the first supporter 14 that fixes the first connector 13 to one side surface of the backing layer 10, the second connector 17 is spaced apart from the first connector 13, and thus the second connector 17 may be electrically isolated from the first connector 13.

According to the present example, the electrode provided on the first connector 13 is a signal electrode, and an electrode provided on the second connector 17 is a ground electrode.

The second connector 17 may also include an insulator and an electrode in the same manner as the first connector 13. The electrode may include a plurality of electrodes aligned on the second connector 17 in the same manner as the first connector 13. Alternatively, the electrode may form the entirety of the second connector 17.

A second supporter 18, which supports the second connector 17 on one side surface thereof, may be installed on the second connector 17 to fix the second connector 17 to one side surface of the backing layer 10. The second supporter 18 may also be formed of an insulating material in the same manner as the first supporter 14.

In addition, a second electrode layer 19 may be disposed on the front surface of the backing layer 10 to be separated from the first electrode layer 15, which is electrically connected to the first connector 13. The second electrode layer 19 is electrically connected to the second connector 17.

According to the present example, a first electrode 21, which is electrically connected to the first electrode layer 15 disposed on the front surface of the backing layer 10, and a second electrode 22, which is electrically connected to the second electrode layer 19 disposed on the front surface of the backing layer 10 to be separated from the first electrode layer 15, are disposed on the piezoelectric layer 20. Here, the first electrode 21 and second electrode 22 are formed to be separated from each other.

In FIGS. 1 and 2, the first electrode 21 is formed on the rear surface of the piezoelectric layer 20, and the second electrode 22 is formed on the front surface of the piezoelectric layer 20. However, according to the embodiment shown in FIGS. 3 and 4, the first electrode 21 and the second electrode 22 are formed on the rear surface of the piezoelectric layer 20 to be separated from each other. In addition, the second electrode 22 extends from the rear surface to the front surface of the piezoelectric layer 20 along the side surfaces of the piezoelectric layer 20.

That is, the first electrode 21 of the piezoelectric layer 20 electrically connected to the first electrode layer 15 is electrically connected to the first connector 13, i.e., a signal electrode. The second electrode 22 of the piezoelectric layer 20 electrically connected to the second electrode layer 19 is electrically connected to the second connector 17, i.e., a ground electrode. As a result, an electrical signal is applied to the piezoelectric layer 20.

The second electrode layer 19 may be disposed on the front surface of the backing layer 10 using a conductive material such as gold, silver, or copper by coating, deposition, sputtering, plating, or spraying.

FIGS. 5 and 6 illustrate an ultrasonic probe according to another example of the present application. Referring to FIGS. 5 and 6, the first connector 13 is installed on at least one side surface of the backing layer 10.

The first connector 13 may include an insulator and an electrode. The electrode may include a plurality of electrodes disposed on the insulator. As shown in FIG. 9, each of the electrodes extends in the z-axis direction. One end of each electrode is exposed through the front surface of the backing layer 10 to be electrically connected to a first electrode layer 15 disposed on the front surface of the backing layer 10. The electrodes may be arranged in the y-axis direction to be spaced apart from each other by a predetermined interval.

In this example, the electrode provided on the first connector 13 is a signal electrode that is electrically connected to the first electrode layer 15 of the backing layer 10 and applies an electrical signal to the piezoelectric layer 20.

After processing of the piezoelectric layer 20 into an array, the number of the electrodes and the interval therebetween may be determined such that each of the electrodes respectively corresponds to each of the elements constituting the array.

The first connector 13 may be installed on at least one side surface of the backing layer 10. In FIG. 6, the first connectors 13 are installed on both side surfaces of the backing layer 10. However, the first connector 13 may be installed on one side surface of the backing layer 10.

If the first connectors 13 are installed on both side surfaces of the backing layer 10, the electrodes of the first connector 13 provided on the left side surface and the electrodes of the first connector 13 provided on the right side surface may be aligned alternately with respect to each other.

Referring to FIG. 10, the electrodes of the first connector 13 provided on the left side surface are aligned alternately with respect to the electrodes of the first connector 13 provided on the right side surface.

FIG. 10 is a top view of the backing layer 10 before the piezoelectric layer 20 is installed. In FIG. 10, the first electrode layer 15 shown in FIGS. 5 and 6 is not illustrated.

As shown in FIG. 10, if the electrodes of the first connectors 13 provided on both side surfaces of the backing layer 10 are aligned alternately with respect to each other, the first connectors 13 are diced along separation lines d shown in FIG. 10, when the piezoelectric layer 20 is installed on the front surface of the backing layer 10 and divided into an array by a dicing process later. Accordingly, each of the electrodes of the first connectors 13 disposed on the left and right side surfaces of the backing layer 10 may be electrically connected to each of the elements of the piezoelectric layer 20.

The first connector 13 may include a flexible printed circuit board (FPCB). The first connector 13 may also include a PCB or other known elements capable of supplying an electrical signal.

In addition, the first electrode layer 15 electrically connected to the first connector 13 installed on one side surface of the backing layer 10 may be disposed on the front surface of the backing layer 10. A first electrode 21 electrically connected to the first electrode layer 15 disposed on the front surface of the backing layer 10 may be disposed on the rear surface of the piezoelectric layer 20.

Thus, the first electrode layer 15 is electrically connected to the first electrode 21 disposed on the rear surface of the piezoelectric layer 20, so that an electrical signal provided from the first connector 13 may be transmitted to the piezoelectric layer 20. Since the electrode of the first connector 13 is a signal electrode, the first electrode 21 disposed on the rear surface of the piezoelectric layer 20 constitutes a signal electrode (or positive electrode)A second electrode 22 to be disposed on the front surface of the piezoelectric layer 20 constitutes a ground electrode (or negative electrode).

The first electrode layer 15 may be disposed on the front surface of the backing layer 10 using a conductive material such as gold, silver, or copper by coating, deposition, sputtering, plating, or spraying.

A first supporter 14, which supports the first connector 13 on the side surface thereof, may be installed on the first connector 13 to fix the first connector 13 to one side surface of the backing layer 10.

The first supporter 14 may be formed of an insulating material.

The first supporter 14 is installed such that a portion of the first supporter 14 is attached to the first connector 13 to fix the first connector 13 to one side surface of the backing layer 10 and another portion of the first supporter 14 protrudes from the front surface of the backing layer 10.

If the first supporters 14 are disposed on both side surfaces of the backing layer 10 to protrude from the front surface of the backing layer 10, mounting grooves providing mounting positions when the piezoelectric layer 20 is installed on the front surface of the backing layer 10 may be formed. That is, the piezoelectric layer 20 is mounted on the backing layer 10 in a space formed by the first supporters 14 installed to protrude from the front surface of the backing layer 10.

A second electrode layer 19 may be disposed on the front surface of the first supporter 14. The second electrode layer 19 may be electrically connected to the second electrode 22 disposed on the front surface of the piezoelectric layer 20. That is, by installing the first supporter 14 such that a protruding height of the first supporter 14 corresponds to a thickness of the piezoelectric layer 20, the first electrode 21 (disposed on the front surface of the piezoelectric layer 20) may be electrically connected to the second electrode layer 19 (disposed on the front surface of the first supporter 14) when the piezoelectric layer 20 is installed on the front surface of the backing layer 10.

As described above, since the first connector 13 that is electrically connected to the first electrode 21 (disposed on the rear surface of the piezoelectric layer 20) functions as a signal electrode, an element, which applies a ground signal, may be electrically connected to the second electrode layer 19 (electrically connected to the second electrode 22 disposed on the front surface of the piezoelectric layer 20).

The second electrode layer 19 may be disposed on the front surface of the backing layer 10 using a conductive material such as gold, silver, or copper by coating, deposition, sputtering, plating, or spraying.

FIGS. 7 and 8 illustrate an ultrasonic probe according to another example. Referring to FIGS. 7 and 8, a first connector 13 and a second connector 17 are disposed on at least one side surface of the backing layer 10.

FIGS. 7 and 8 illustrate that the first connectors 13 are installed on both side surfaces of the backing layer 10, as shown in FIGS. 5 and 6. However, the first connector 13 may be installed on one side surface of the backing layer 10.

The first connector 13 and a first supporter 14 are the same as those of FIGS. 5 and 6, and thus a detailed description thereof is omitted.

In the ultrasonic probe of this example, the second connector 17 is further installed on at least one side surface of the backing layer 10. The second connector 17 is installed to be spaced apart from the first connector 13 by a predetermined interval.

By installing the second connector 17 on the first supporter 14 that fixes the first connector 13 to one side surface of the backing layer 10, the second connector 17 is spaced apart from the first connector 13. Thus the second connector 17 may be electrically isolated from the first connector 13.

As shown in the drawings, by installing the second connector 17 on the first supporter 14 protruding from the front surface of the backing layer 10, the second connector 17 also protrudes from the front surface of the backing layer 10 along with the first supporter 14.

According to the present example, an electrode provided on the first connector 13 is a signal electrode, and an electrode provided on the second connector 17 is a ground electrode.

The second connector 17 may also include an insulator and an electrode in the same manner as the first connector 13. The electrode may include a plurality of electrodes aligned on the second connector 17 in the same manner as the first connector 13, or the electrode may form the entirety of the second connector 17.

A second supporter 18, which supports the second connector 17 on one side surface thereof, may be installed on the second connector 17 to fix the second connector 17 to one side surface of the backing layer 10. The second supporter 18 may also be formed of an insulating material in the same manner as the first supporter 14.

In addition, as shown in the drawings, the second supporter 18 may be attached to the second connector 17 to protrude from the front surface of the backing layer 10 in the same manner as the first supporter 14.

A second electrode layer 19 is disposed on the front surface of the first supporter 14 to be electrically connected to the second connector 17.

In the same manner as the embodiment shown in FIGS. 5 and 6, in FIGS. 7 and 8, a first electrode 21 formed on the rear surface of the piezoelectric layer 20 is electrically connected to a first electrode layer 15 formed on the front surface of the backing layer 10, and a second electrode 22 formed on the front surface of the piezoelectric layer 20 is electrically connected to the second electrode layer 19 formed on the front surface of the first supporter 14.

In other words, the first electrode 21 of the piezoelectric layer 20 electrically connected to the first electrode layer 15 is electrically connected to the first connector 13, i.e., a signal electrode. The second electrode 22 of the piezoelectric layer 20 electrically connected to the second electrode layer 19 is electrically connected to the second connector 17, i.e., a ground electrode. As a result, an electrical signal is applied to the piezoelectric layer 20.

The second electrode layer 19 may be disposed on the front surface of the backing layer 10 using a conductive material such as gold, silver, or copper by a coating, deposition, sputtering, plating, or spraying process.

Figure 11:
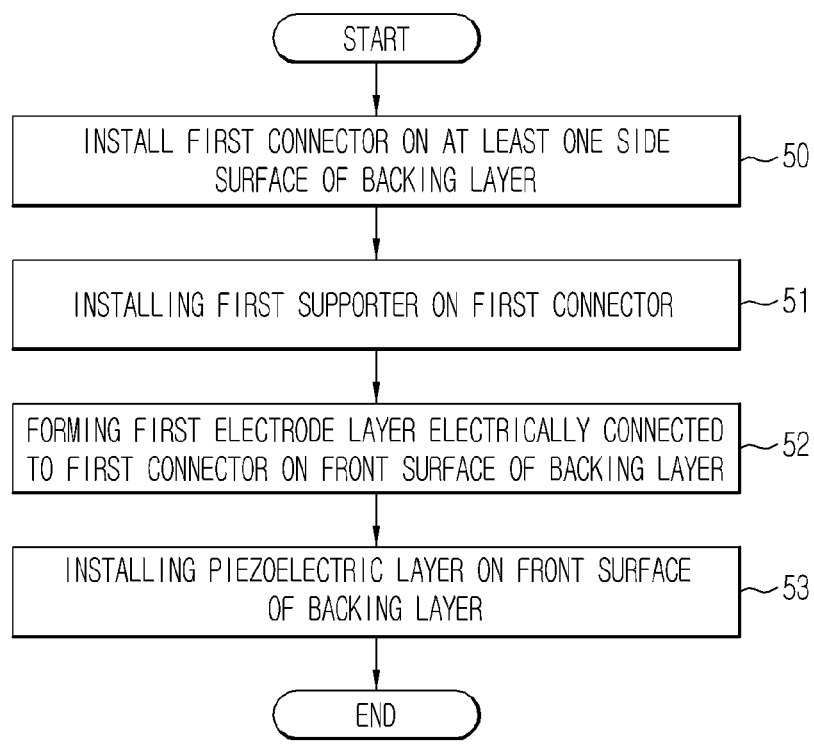
FIG. 11 is a flowchart illustrating a method of manufacturing an ultrasonic probe according to an example of the present application.

FIG. 11 is a flowchart illustrates an example of a method of manufacturing an ultrasonic probe.

A first connector 13 is installed on at least one side surface of a backing layer 10 (Operation 50).

The first connector 13 may include an insulator and an electrode 31. The electrode 31 may include a plurality of electrodes disposed on the insulator. As shown in FIG. 9, each of the electrodes 31 extends in the z-axis direction. One end of each electrode 31 is exposed through the front surface of the backing layer 10 to be electrically connected to a first electrode layer 15 disposed on the front surface of the backing layer 10. The electrodes 31 may be arranged in the y-axis direction to be spaced apart from each other by a predetermined interval.

In this example, the electrode 31 provided on the first connector 13 is a signal electrode.

In addition, the first connectors 13 may be installed on both side surfaces of the backing layer 10. The first connector 13 may include a flexible printed circuit board (FPCB). The first connector 13 may also include a PCB or other known elements capable of supplying an electrical signal.

After installation of the first connector 13, a first supporter 14, which supports the first connector 13, is attached to the first connector 13 to fix the first connector 13 to one side surface of the backing layer 10 (Operation 51).

The first supporter 14 may be formed of an insulating material.

After attachment of the first supporter 14, the first electrode layer 15 is disposed on the front surface of the backing layer 10 to be electrically connected to the first connector 13 (Operation 52).

The first electrode layer 15 may be disposed on the front surface of the backing layer 10 using a conductive material such as gold, silver, or copper by coating, deposition, sputtering, plating, or spraying.

After formation of the first electrode layer 15, a piezoelectric layer 20 including a first electrode 21 and a second electrode 22 respectively formed on the rear and front surfaces thereof is installed on the front surface of the backing layer 10 (Operation 53).

According to the present example, the electrode 31 provided on the first connector 13 is a signal electrode that is electrically connected to the first electrode layer 15 of the backing layer 10 and applies an electrical signal to the piezoelectric layer 20. Thus, the first electrode 21 disposed on the rear surface of the piezoelectric layer 20 constitutes a signal electrode.

Figure 12:
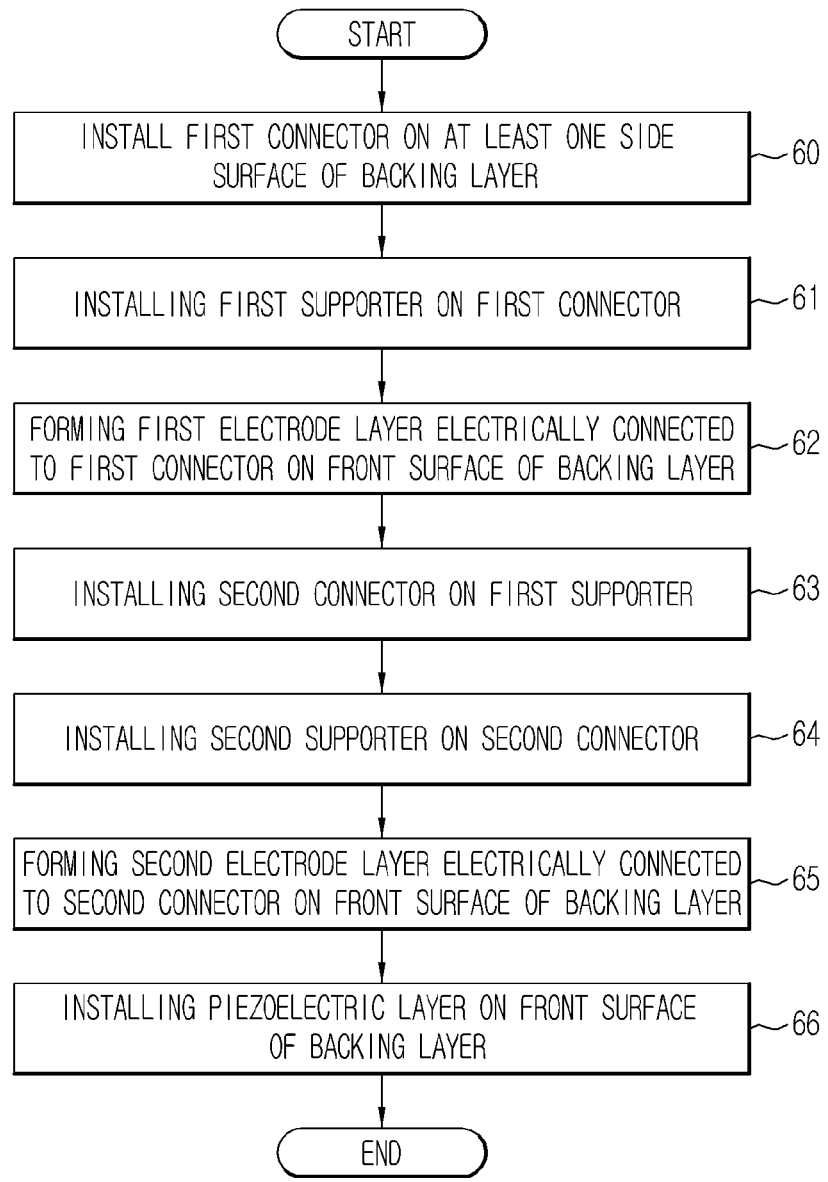
FIG. 12 is a flowchart illustrating a method of manufacturing an ultrasonic probe according to another example of the present application.

FIG. 12 is a flowchart illustrating another method of manufacturing an ultrasonic probe.

The process of FIG. 12 is identical to that of FIG. 11 until the first connector 13, the first supporter 14, and the first electrode layer 15 are formed, and thus a detailed description of Operations 60 to 62 will be omitted.

A second connector 17 is installed on at least one side surface of the backing layer 10 (Operation 63).

The second connector 17 is installed to be spaced apart from the first connector 13 by a predetermined interval.

By installing the second connector 17 on the first supporter 14 that fixes the first connector 13 to one side surface of the backing layer 10, the second connector 17 is spaced apart from the first connector 13, and thus the second connector 17 may be electrically isolated from the first connector 13.

According to the present example, the electrode provided on the first connector 13 is a signal electrode, and an electrode provided on the second connector 17 is a ground electrode.

The second connector 17 may also include an insulator and an electrode in the same manner as the first connector 13. The electrode may include a plurality of electrodes aligned on the second connector 17 in the same manner as the first connector 13, or the electrode may form the entirety of the second connector 17.

After installation of the second connector 17, a second supporter 18, which supports the second connector 17, is attached to the second connector 17 to fix the second connector 17 to one side surface of the backing layer 10 (Operation 64).

The second supporter 18 may be formed of an insulating material in the same manner as the first supporter 14.

After attachment of the second supporter 18, a second electrode layer 19 electrically connected to the second connector 17 is installed on the front surface of the backing layer 10 to be isolated from the first electrode layer 15 (Operation 65).

That is, the second electrode layer 19 is formed to be isolated from the first electrode layer 15 electrically connected to the first connector 13, and the second electrode layer 19 is electrically connected to the second connector 17.

The second electrode layer 19 may be disposed on the front surface of the backing layer 10 using a conductive material such as gold, silver, or copper by a coating, deposition, sputtering, plating, or spraying process.

After formation of the second electrode layer 19, a piezoelectric layer 20 provided with a first electrode 21 and a second electrode 22, which are separated from each other and respectively electrically connected to the first electrode layer 15 and the second electrode layer 19, is installed on the front surface of the backing layer 10 (Operation 66).

According to the present example, a first electrode 21, which is electrically connected to the first electrode layer 15 disposed on the front surface of the backing layer 10, and a second electrode 22, which is electrically connected to the second electrode layer 19 disposed on the front surface of the backing layer 10 to be separated from the first electrode layer 15, are disposed on the piezoelectric layer 20. Here, the first electrode 21 and second electrode 22 are formed to be separated from each other.

According to another example, the first electrode 21 is disposed on the rear surface of the piezoelectric layer 20, and the second electrode 22 is disposed on the front surface of the piezoelectric layer 20. However, the first electrode 21 and the second electrode 22 are disposed on the rear surface of the piezoelectric layer 20 such that the first electrode 21 is separated from the second electrode 22. In addition, the second electrode 22 extends from the rear surface to the front surface of the piezoelectric layer 20 along the side surfaces of the piezoelectric layer 20.

That is, the first electrode 21 of the piezoelectric layer 20 electrically connected to the first electrode layer 15 is electrically connected to the first connector 13, i.e., a signal electrode. The second electrode 22 of the piezoelectric layer 20 electrically connected to the second electrode layer 19 is electrically connected to the second connector 17, i.e., a ground electrode. As a result, an electrical signal is applied to the piezoelectric layer 20.

Figure 13:
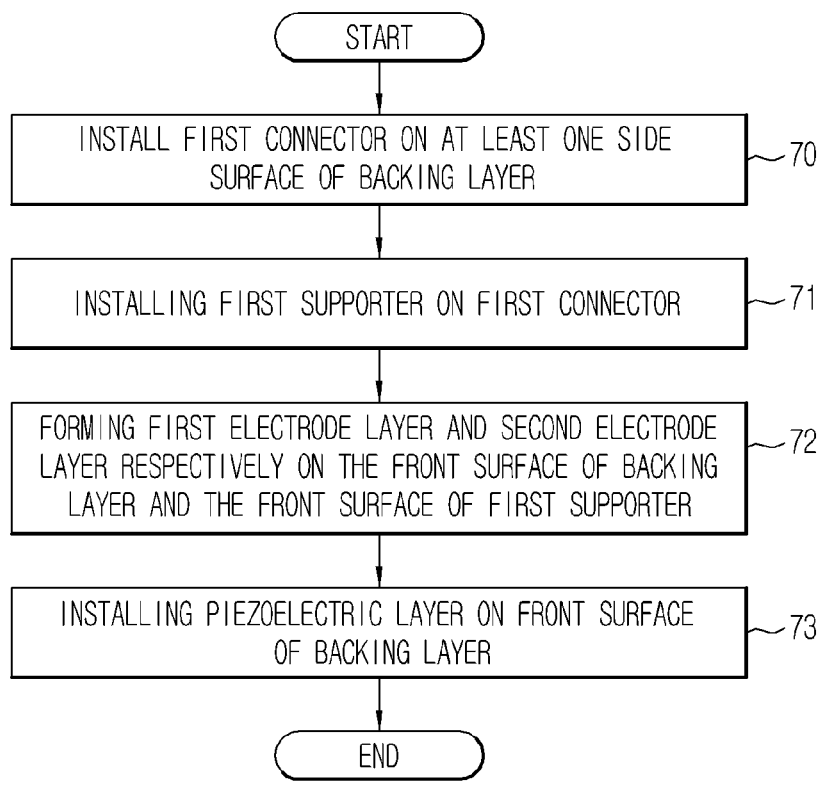
FIGS. 13 and 14 are flowcharts illustrating methods of manufacturing ultrasonic probes according to another example of the present application.

FIG. 13 is a flowchart illustrating another method of manufacturing an ultrasonic probe.

A first connector 13 is installed on at least one side surface of a backing layer 10 (Operation 70).

The first connector 13 may include an insulator and an electrode. The electrode may include a plurality of electrodes disposed on the insulator. As shown in FIG. 9, each of the electrodes extends in the z-axis direction. One end of each electrode is exposed through the front surface of the backing layer 10 to be electrically connected to a first electrode layer 15 disposed on the front surface of the backing layer 10. The electrodes may be arranged in the y-axis direction to be spaced apart from each other by a predetermined interval.

According to the present example, the electrode provided on the first connector 13 is a signal electrode.

In addition, the first connectors 13 may be installed on both side surfaces of the backing layer 10 or on one side surface of the backing layer 10. The first connector 13 may include a flexible printed circuit board (FPCB). The first connector 13 may also include a PCB or other known elements capable of supplying an electrical signal.

After installation of the first connector 13, a first supporter 14, which supports the first connector 13, is attached to the first connector 13 to fix the first connector 13 to one side surface of the backing layer 10 (Operation 71).

The first supporter 14 is installed such that a portion of the first supporter 14 is attached to the first connector 13 to fix the first connector 13 to one side surface of the backing layer 10 and another portion of the first supporter 14 protrudes from the front surface of the backing layer 10. In addition, the first supporter 14 may be formed of an insulating material.

After attachment of the first supporter 14, a first electrode layer 15 is disposed on the front surface of the backing layer 10 to be electrically connected to the first connector 13, and a second electrode layer 19 is disposed on the front surface of the first supporter 14 (Operation 72).

The first electrode layer 15 and the second electrode layer 19 may be disposed on the front surface of the backing layer 10 using a conductive material such as gold, silver, or copper by coating, deposition, sputtering, plating, or spraying.

After formation of the first electrode layer 15 and the second electrode layer 19, a piezoelectric layer 20 provided with a first electrode 21 and a second electrode 22 respectively on the front and rear surfaces thereof is installed on the front surface of the backing layer 10 (Operation 73).

In this example, the electrode provided on the first connector 13 is a signal electrode that is electrically connected to the first electrode layer 15 of the backing layer 10 and applies an electrical signal to the piezoelectric layer 20. Thus, the first electrode 21 disposed on the rear surface of the piezoelectric layer 20 constitutes a signal electrode. The second electrode 22 disposed on the front surface of the piezoelectric layer 20 constitutes a ground electrode. The second electrode 22 disposed on the front surface of the piezoelectric layer 20 is electrically connected to the second electrode layer 19 disposed on the front surface of the first supporter 14.

Figure 14:
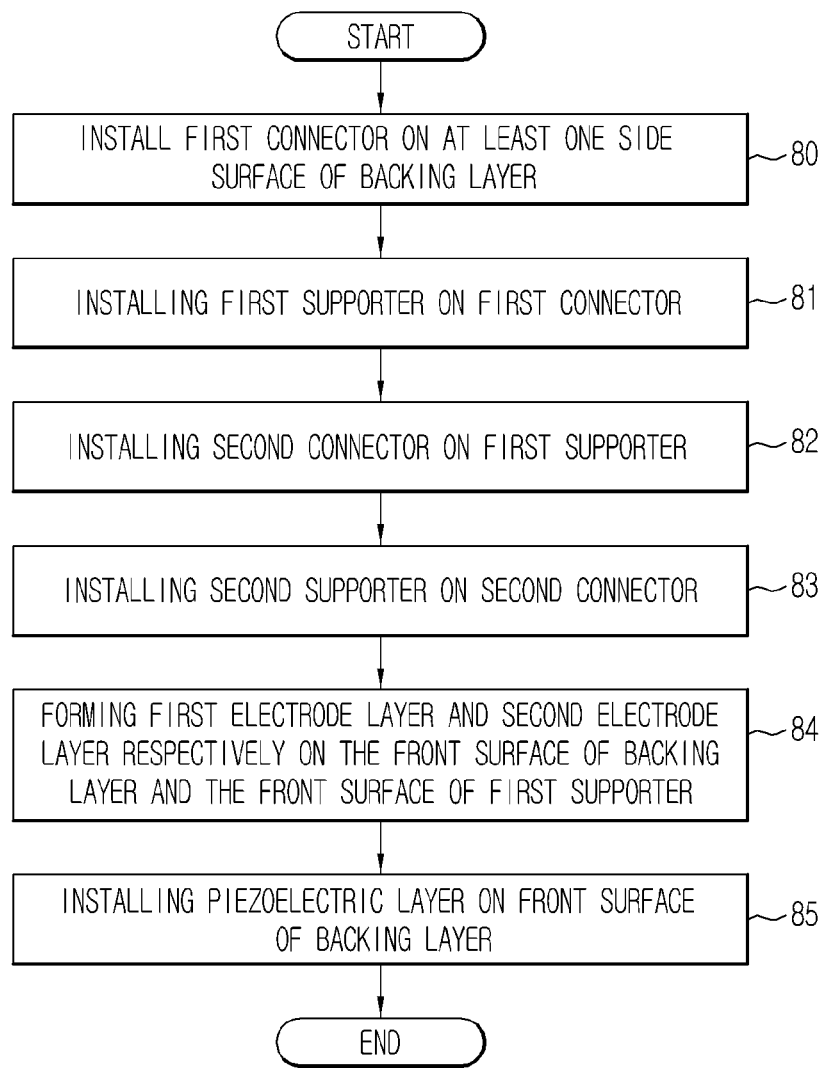

FIG. 14 is a flowchart illustrating another example of a method of manufacturing an ultrasonic probe.

The process of FIG. 14 is identical to that of FIG. 13 until the first connector 13 and the first supporter 14 are formed, and thus a detailed description of Operations 80 and 81 will be omitted.

A second connector 17 is installed on at least one side surface of the backing layer 10 (Operation 82).

The second connector 17 is installed to be spaced apart from the first connector 13 by a predetermined interval.

By installing the second connector 17 on the first supporter 14 that fixes the first connector 13 to one side surface of the backing layer 10, the second connector 17 is spaced apart from the first connector 13, and thus the second connector 17 may be electrically isolated from the first connector 13.

The electrode provided on the first connector 13 is a signal electrode, and an electrode provided on the second connector 17 is a ground electrode.

The second connector 17 may also include an insulator and an electrode in the same manner as the first connector 13. The electrode may include a plurality of electrodes aligned on the second connector 17 in the same manner as the first connector 13, or the electrode may form the entirety of the second connector 17.

After installation of the second connector 17, a second supporter 18, which supports the second connector 17, is installed on the second connector 17 to fix the second connector 17 to one side surface of the backing layer 10 (Operation 83).

The second supporter 18 is attached to the second connector 17 to protrude from the front surface of the backing layer 10 in the same manner as the first supporter 14 as shown in FIG. 13. The second supporter 18 may be formed of an insulating material in the same manner as the first supporter 14.

After attachment of the second supporter 18, a first electrode layer 15 is disposed on the front surface of the backing layer 10 to be electrically connected to the first connector 13, and a second electrode layer 19 is installed on the front surface of the first supporter 14 to be electrically connected to the second connector 17 (Operation 84).

That is, the first electrode layer 15 installed to be electrically connected to the first connector 13 is electrically separated from the second electrode layer 19 installed to be electrically connected to the second connector 17.

The second electrode layer 19 may be disposed on the front surface of the backing layer 10 using a conductive material such as gold, silver, or copper by coating, deposition, sputtering, plating, or spraying.

After formation of the first electrode layer 15 and the second electrode layer 19, a piezoelectric layer 20 provided with a first electrode 21 and a second electrode 22, which are separated from each other and respectively electrically connected to the first electrode layer 15 and the second electrode layer 19, is installed on the front surface of the backing layer 10 (Operation 85).

The first electrode 21 disposed on the rear surface of the piezoelectric layer 20 is electrically connected to the first electrode layer 15 disposed on the front surface of the backing layer 10, and the second electrode 22 disposed on the front surface of the piezoelectric layer 20 is electrically connected to the second electrode layer 19 disposed on the front surface of the first supporter 14.

That is, the first electrode 21 of the piezoelectric layer 20 electrically connected to the first electrode layer 15 is electrically connected to the first connector 13, i.e., a signal electrode. The second electrode 22 of the piezoelectric layer 20 electrically connected to the second electrode layer 19 is electrically connected to the second connector 17, i.e., a ground electrode. As a result, an electrical signal is applied to the piezoelectric layer 20.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. An ultrasonic probe comprising:
   a piezoelectric material;
   a backing layer installed on a rear surface of the piezoelectric material;

a first connector installed on at least one side surface of an outside of the backing layer, the first connector being electrically connected to an electrode of the piezoelectric material;

a first electrode layer covering the first connector and the backing layer;

a first supporter installed on the first connector to support the first connector by fixing the first connector to one side surface of the backing layer, the first supporter is connected to a side of the first electrode layer and the first connector;

a second connector connected to a side of the first supporter;

a second supporter connected to a side of the second connector; and a second electrode layer covering an entire top surface of the first supporter.

2. The ultrasonic probe according to claim 1, wherein the first electrode layer is disposed on a front surface of the backing layer, and wherein the first electrode layer is electrically connected to the first connector.

3. The ultrasonic probe according to claim 2, wherein the piezoelectric material comprises an electrode disposed on at least one surface of the piezoelectric material comprising the rear surface of the piezoelectric material and electrically connected to the first electrode layer.

4. The ultrasonic probe according to claim 1, wherein the first supporter comprises an insulating material.

5. The ultrasonic probe according to claim 1, wherein the second connector is installed to be spaced apart from the first connector and electrically connected to the piezoelectric material.

6. The ultrasonic probe according to claim 5, wherein the second supporter is installed on the second connector and supports the second connector to fix the second connector to one side surface of the first supporter, and wherein the second supporter comprises an insulating material.

7. The ultrasonic probe according to claim 5, wherein the first connector and the second connector comprise a flexible printed circuit board (FPCB), a printed circuit board (PCB), or a wire.

8. The ultrasonic probe according to claim 5, wherein the second electrode layer is disposed on a front surface of the backing layer, and wherein the second electrode layer is electrically connected to the second connector.

9. The ultrasonic probe according to claim 8, wherein the piezoelectric material comprises an electrode disposed on at least one surface of the piezoelectric material comprising a rear surface of the piezoelectric material and electrically connected to the second electrode layer.

10. The ultrasonic probe according to claim 8, wherein the first electrode layer is disposed on a front surface of the backing layer and electrically connected to the first connector, and wherein the first electrode layer is separated from the second electrode layer.

11. The ultrasonic probe according to claim 1, wherein the first supporter includes material that is different from the backing layer.

* * * * *